United States Patent [19]

Gorenstein et al.

[11] Patent Number: 5,218,088
[45] Date of Patent: Jun. 8, 1993

[54] PROCESS FOR PREPARING DITHIOPHOSPHATE OLIGONUCLEOTIDE ANALOGS VIA NUCLEOSIDE THIOPHOSPHORAMIDITE INTERMEDIATES

[75] Inventors: David Gorenstein, Carmel; Nassar Farschtschi, West Lafayette, both of Ind.

[73] Assignee: Purdue Research Foundation, West Lafayette, Ind.

[21] Appl. No.: 430,733

[22] Filed: Nov. 2, 1989

[51] Int. Cl.$^5$ ..................... C07H 19/10; C07H 19/20
[52] U.S. Cl. ............................. 536/25.34; 536/25.31
[58] Field of Search ................ 536/27, 28, 29; 558/95

[56] References Cited

U.S. PATENT DOCUMENTS 4,668,777  5/1987  Caruthers et al. ................ 536/27

OTHER PUBLICATIONS

"Deoxynucleoside Phosphoramidites—A New Class Of Key Intermediates For Deoxypolynucleotide Synthesis", *Tetrahedron Letters*, vol. 22, No. 20, pp. 1859–1862, 1981, Beaucage et al.
"An Investigation Of Several Deoxynucleoside Phosphoramidites Useful For Synthesizing Deoxyolignucleotides", McBride et al., *Tetrahedron Letters*, vol. 24, No. 3, pp. 245–248, 1983.
"Synthesis Of Dinucleoside Phosphorodithioates Via Thioamidites", Brill, et al., *Tetrahedron Letters*, vol. 29, No. 43 pp. 5517–5520, 1988.
"Synthesis Of Oligodeoxynucletides Containing Specific Methylphosphonothioate and Dithioate Moieties", Brill, et al., Aug. 8–12, 1988.
"Preparation Of A Deoxynucleside Thiophosphoramidite Intermediate In The Synthesis Of Nucleoside Phosphorodithioates", Faraschtschi & Gorenstein, *Tetrahedron Letters*, vol. 29, No. 52, pp. 6843–6846, 1988.
"Synthesis Of Oligodeoxynucleoside Phosphorodithioates Via Thioamidites", Brill, et al., *J. Amer. Chem. Soc.*, 1989, vol. 111, pp. 2321–2322.
Chemical Abstracts No. 107:198467b, Al'fonsov et al. Zh. Obshch. Khim, 56(8), 1697–1699 (1986).
Chemical Abstracts No. 96:85bb8d, Sinyashin et al. Zh. Obshch. Khim. 51(11), 2410–2413, (1981).

*Primary Examiner*—Johnnie R. Brown
*Assistant Examiner*—Gary L. Kunz
*Attorney, Agent, or Firm*—Barnes & Thornburg

[57] ABSTRACT

A method for synthesis of oligonucleotide analogs having dithiophosphate internucleosidic linkages is described. Monohalohydrocarbylthiophosphoramidites are utilized to prepare nucleoside thiophosphoramidite intermediates which are activated for nucleoside coupling with tetrazole catalysts. Sulfur oxidation and dehydrocarbylation of the coupled thiophosphite intermediates provide oligonucleotide analogs having achiral dithiophosphate internucleosidic linkages.

4 Claims, 2 Drawing Sheets

PROCESS FOR PREPARING DITHIOPHOSPHATE OLIGONUCLEOTIDE ANALOGS VIA NUCLEOSIDE THIOPHOSPHORAMIDITE INTERMEDIATES

FIELD OF THE INVENTION

This invention relates to the synthesis of oligonucleotide analogs having dithiophosphate internucleosidic linkages. More particularly, this invention relates to an improved process utilizing nucleoside phosphoramidite intermediates in the synthesis of nucleoside phosphorodithioates. Novel monohalohydrocarbyl thiophosphoramidites are useful intermediates for the synthesis of 3'-O-hydrocarbyl thiophosphoramidite nucleosides activated for coupling with nucleosides or oligonucleosides or analogs thereof using mildly acidic nitrogenous catalysts such as tetrazole.

BACKGROUND AND SUMMARY OF THE INVENTION

One of the most widely employed methods of synthesizing oligonucleotides is known as the phosphate triester method. The phosphate triester method can be employed in solution, and generally involves coupling of a protected nucleoside 3'-phosphate with another protected nucleoside having a 5'-hydroxyl group. The coupled reaction product is typically isolated/purified chromatographically and one of the protecting groups is removed to yield a dimer block. The dimer block can then be coupled with other selected oligomeric blocks having an unprotected 3'-phosphate or 5'-hydroxyl terminus to yield oligomers having desired nucleoside sequences.

The phosphate triester method for oligonucleotide synthesis can also be readily adapted for solid phase reaction conditions. Thus a 5'-O-protected deoxyribonucleoside, for example, can be covalently attached to a solid support, such as polystyrene, cellulose, or silica gel, and subjected to a sequence of reaction conditions which first effects removal of the 5'-O-protecting group and thereafter couples the support bound nucleoside to other nucleosides. Repeating the process with selected reactive nucleosides, dimer blocks, or oligonucleotide intermediates enables extension of the nucleotide chain to a predetermined length/composition. In the final step the oligonucleotide is cleaved from the solid support and subjected to conventional purification techniques.

The present invention allows application of such solid phase synthesis procedures to the synthesis of phosphorodithioate oligonucleotide analogs.

Matsukura et al., *Proc. Natl. Acad. Sci.*, Vol. 84, pp. 7706–7710, 1987, have shown that phosphorothioate analogs of oligonucleotides are effective inhibitors of HIV replication and are cytopathic to virally infected T cells. They exhibit antiviral activity in vivo by binding with either the RNA template derived from a virus or duplex DNA derived from a virus that has integrated into the genome of the host. Both complementary "antisense" oligonucleotide phosphorothioates and homooligomer analogs exhibited potent anti-HIV activity. The most effective analog was reported to be a 28-mer oligodeoxycytidine phosphorothioate (S-dC$_{28}$) which exhibited anti-HIV activity at 1 $\mu$M concentration and inhibited de novo DNA synthesis. The authors reported that the S-analogs of deoxyribonucleotides (phosphorothioates) showed no significant degradation over a period of weeks in their cytopathic assay and during incubation in human serum at 37° C. Hydrolysis of normal oligonucleotides indicated a half-life of ~17 hr in the in vitro assay. The S-analogs also showed good permeability to the target cells. Using $^{35}$S-labeled phosphorothioates, S-dC$_{28}$ showed significant amounts of radioactivity in the immortalized T4+ ATH8 and H9 cells within several minutes.

Notably, however, the phosphorothioate linkages of oligonucleotide analogs as disclosed by Matsukura et al. are chiral structures. In the best of circumstances one might be able to achieve >99% yields in the nucleotide chain assembly steps during solid-phase synthesis. Yet, if a coupling reaction proceeds with no stereospecificity, only 50% of the dimer product will have the correct stereochemistry. Thus, for example, in the synthesis of an n-mer having chiral phosphorothioate internucleosidic linkages, the best theoretical yield of diastereomerically pure n-mer, would be $\frac{1}{2}^{n-1}$ (<3% for a 6-mer and <1.0% yield for an 8-mer). This highlights the importance of avoiding phosphorothioate or other chiral centers in oligonucleotide analogs. Use of achiral internucleosidic linkages in the construction of nucleotide analogs not only avoids yield loss due to unwanted diastereomeric by-products, but also eliminates need for complex separation of diastereomers.

It is therefore an object of the present invention to provide a method for synthesis of achiral dithiophosphate oligonucleotide analogs.

It is a further object of the invention to provide novel monohalohydrocarbyl thiophosphoramidites as intermediates for the synthesis of achiral analogs of oligonucleotides.

Yet another object of the invention is the use of tetrazole or other acidic pKa nitrogenous compounds to catalyze the production of thiophosphite coupled nucleosides by the reaction of nucleoside 3'-O-thiophosphoramidites with nucleoside 5'-hydroxyl groups.

In accordance with the foregoing objectives a method is provided for the synthesis of intermediates useful for producing achiral phosphorodithioate analogs of oligonucleotides. The unprotected 3'-hydroxyl group of a nucleoside (hereinafter meaning nucleoside or deoxynucleoside) or oligonucleoside (that term hereinafter inclusive of oligonucleotides, oligodeoxynucleotides, and analogs thereof having internucleosidic linkages other than phosphate) is coupled with a halohydrocarbylthiophosphoramidite to provide a nucleoside 3'-O-hydrocarbylthiophosphoramidite. That product is reacted with a nucleoside or an oligonucleoside having an unprotected 5'-hydroxyl group and a protected 3'-hydroxyl group in the presence of a weak nitrogenous acid having a pKa equal to or greater to the pKa of 1H-tetrazole to provide nucleosides coupled through a 3', 5' hydrocarbyl thiophosphite linkage. Oxidation of that coupled oligonucleside analog with sulfur converts the thiophosphite to a dithioate triester coupled oligonucleotide. Deprotection of the 3'-hydroxyl group, removal of the hydrocarbyl moiety, and repetition of the synthesis scheme allows construction of a nucleoside oligomers having achiral phosphorodithioate internucleosidic linkages.

In a preferred embodiment of the present invention, a monochloro-N,N-dialkylaminohydrocarbylthiophosphine is used to form the reactive nucleoside 3'-O-hydrocarbylthiophosphoramidite. Most preferred mono-chloro-N,N-dialkylaminohydrocarbylthiophosphine intermediates are those wherein the N,N-dialkylamino group is N,N-diisopropyl, N,N-dimethyl, or morpholino, and the hydrocarbylthio group is methylthio, benzylthio, chlorobenzylthio, or dichlorobenzylthio.

The intermediate nucleoside 3'-O-thiophosphoramidite can be coupled by reaction with a nucleoside or oligonucleoside having an unprotected 5'-hydroxyl group and a protected 3'-hydroxyl group in the presence of 1H-tetrazole. Oxidation of the coupled oligonucleoside analog with sulfur in the presence of a tertiary amine base, preferably pyridine or 2,6-lutidine, followed by removal of the hydrocarbyl moiety through reaction with sulfur nucleophiles such as thiophenol provides dimers or oligomers having a phosphorodithioate internucleosidic linkage.

Deprotection of the 5'-hydroxyl group of the resulting oligomer and repetition of the aforedescribed synthesis scheme allows for facile synthesis of dithiophosphate coupled oligonucleotide analogs having a predetermined oligonucleotide sequence. Thus by using appropriate reaction sequences of oligodeoxynucleotide analogs (again, including oligodeoxynucleotide analogs) in a predetermined combination of phosphorodithioate and, for example, natural phosphate or other linkages can be synthesized.

Oligonucleotide analogs having a phosphorodithioate linkages are of potential use for both therapeutic and diagnostic applications. Phosphorodithioate linked oligonucleotides are isosteric and isopolar with normal phosphodiester linkages and are expected to have other biochemical and biophysical properties similar to natural DNA. Such DNA analogs are expected to be relatively nuclease resistant and easily derivatized with reporter groups, two very significant chemical properties important for numerous biochemical and biological applications. Therapeutically, phosphorodithioate oligonucleotide analogs can also be used as antisense agents directed against foreign or aberrant genetic elements such as virally derived nucleic acids or mRNA of oncogenic or other undesired genetic elements. Dithiophosphate analogs of ribozymes can also be produced that could catalytically cleave mRNA of viral, bacterial, or oncogenic origin in addition to mRNA derived from any other undesired genetic elements.

BRIEF DESCRIPTION OF THE DRAWINGS

The following detailed description of the invention refers particularly to the accompanying drawings in which.

DETAILED DESCRIPTION OF THE INVENTION

This invention provides novel halophosphoramidite intermediates and an improved method for preparing 3',5'-dinucleoside hydrocarbylthiophosphite, precursors to biologically significant achiral oligonucleotides having phosphorodithioate internucleosidic linkages.

Figure 1:
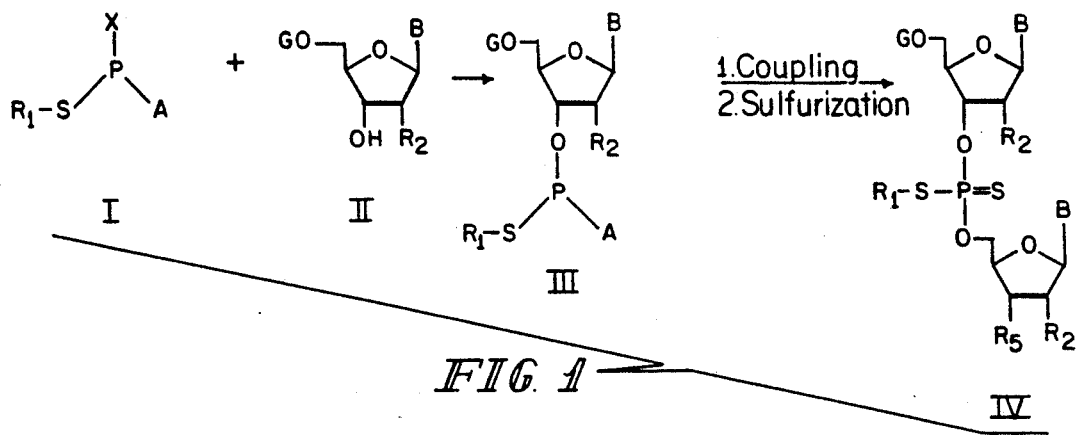
FIG. 1 illustrates the conversion of a monohalohydrocarbylthiophosphoramidite (Formula I) to a dinucleoside dithiophosphate triester (Formula IV)

With reference to FIG. 1, there is provided a monohalohydrocarbylthiophosphoramidite of Formula I wherein X is halo, preferably chloro or bromo, $R_1$ is a hydrocarbyl radical containing up to 10 carbon atoms, and A is a secondary amino group. Phosphoramidite I is typically prepared via a dihalophosphoramidite intermediate formed by reacting the corresponding phosphorus trihalide with two equivalents of the corresponding secondary amine. Conversion of the dihalophosphoramidite intermediate to I is accomplished by reacting it with a sodium salt of the corresponding thiohydrocarboxide in the presence of aluminum trichloride and potassium iodide.

In Formula I, A is preferably a group of the formula $-NR_3R_4$ wherein $R_3$ and $R_4$, taken separately, each represents alkyl, aralkyl, cycloalkyl and cycloalkylalkyl containing up to 10 carbon atoms or $R_3$ and $R_4$, when taken together with the nitrogen atom to which they are attached, form a 5' or 6'-membered ring. Secondary means for which the group $-NR_3R_4$ include a wide variety of saturated secondary amines such as dimethylamine, diethylamine, diisopropylamine, dibutylamine, methylpropylamine, methylhexylamine, methylcyclopropylamine, ethylcyclohexylamine, methylbenzylamine, methylcyclohexylmethylamine, butylcyclohexylamine, morpholine, thiomorpholine, pyrrolidine, piperidine, 2,6-dimethylpiperidine, piperizine and similar saturated monocyclic nitrogen heterocycles. Preferably A in Formula I is either diisopropylamino or morpholino, both of which groups have been found to enhance the stability of the halophosphoramidite of Formula I presumably due to the high degree of steric hindrance about the nitrogen atom. The compounds of Formula I wherein X is the chloro, and wherein A is either diisopropyl or morpholino, are easily purified by distillation and exhibit good stability in solution. In the compounds of Formula I, $R_1$ is generally specified herein as a hydrocarbyl radical containing up to 10 carbon atoms. Such hydrocarbyl radicals include alkyl, aralkyl, cycloalkyl and cycloalkylalkyl containing up to 10 carbon atoms. For use in accordance with the present invention, the nature of the group $R_1$ is not critical to use of the intermediate. Thus $R_1$ can be selected from the group consisting of $C_1-C_{10}$ alkyl, $C_1-C_{10}$ alkenyl, benzyl, chlorobenzyl, dichlorobenzyl, methylbenzyl, chloromethylbenzyl, and cyclohexyl. Preferred $R_1$ groups include $C_1-C_4$ alkyl such as methyl, ethyl, propyl, and butyl, $C_3-C_1$ alkenyl, including allyl, 2-butenyl, benzyl, chlorobenzyl, and dichlorobenzyl. Most preferred groups, because of their ability to be cleaved from a derivative of the halophosphoramidite, a dinucleoside dithiophosphate triester (Formula IV in FIG. 1) are methyl, chlorobenzyl and dichlorobenzyl.

Halothio-phosphoramidite I readily reacts with an unprotected 3'-hydroxyl group of a 5'-protected hydroxyl nucleoside such as represented by Formula II in FIG. 1. "Nucleoside", as it is used herein to define this invention, shall refer to deoxynucleosides, ribonucleosides, and deoxyribonucleosides, nucleosides with modified heterocyclic substituents at the ring nitrogen atoms, nucleosides with substituted exocyclic groups, ring analogs of purines or pyrimidines, and nucleotides having altered sugars or N-glycosidic linkages.

In FIG. 1 G is selected from the group consisting of a hydroxyl protecting group, a solid support, a nucleoside, and a nucleotide; $R_2$ is hydrogen (representing a deoxynucleoside) or a protected hydroxyl group; $R_5$ is hydroxyl, protected hydroxyl or a covalently bound solid support. B is an amino protected base including purine, pyrimidine, purines and pyrimidines modified by exocyclic substituents, ring analogs of purines or pyrimidines, and purines or pyrimidines substituted at ring nitrogen atoms. Most preferably, "B" is an amino-protected base selected from the group consisting of adenine, thymine, cytosine, guanine, uracil, and hypoxanthine.

"Amino-protected" as used herein indicates that the exocyclic amino groups on said bases are covalently bonded to a readily removable amino protecting group. Such groups, means for their application and removal, and their properties under various reaction conditions are known in the art. The benzoyl group is commonly used on adenine and cytosine while the isobutyl group is often used to protect the exocyclic amino group of guanine. The nature of amino protecting groups are not critical so long as they are stable under the reaction conditions of the present process and removable from the product oligonucleoside analogs under conditions not causing degradation of the product itself.

Suitable hydroxyl protecting groups include those covalently bound groups which can be coupled and removed under art-recognized reaction conditions. Suitable hydroxyl protecting groups include trityl, methoxytrityl, dimethoxytrityl, dialkylphosphate, pivaloyl, isobutyloxycarbonyl, t-butyldimethylcylo, tetrahydropyranyl, trialkylsialyl and N-acetyl. As with the amino protecting groups discussed above, the nature of the hydroxyl protecting group utilized to protect the 5'-hydroxyl (or the 2'-hydroxyl in the case of nucleosides) is not critical so long as the protecting group is stable under the conditions of the synthesis process, yet can be removed following completion of the coupling reactions under conditions which do not effect degradation of the coupled oligomer.

As discussed above in FIG. 1, both G and $R_5$ can represent a solid support. Many solid supports are known in the art and include polymers, silica or silica gel having functional groups capable of covalent bonding to the 5' or 3' positions. It should be understood that the group represented by G or $R_5$ include art-recognized covalent linkers for covalent attachment to solid supports such as long-chain alkyl amino groups or other easily derivatized chemical coupling functionalities. Where the group G or $R_5$ in FIG. 1 is a nucleoside or oligonucleoside, it is understood that such entities are bonded to the nucleoside sugar through natural phosphate diester bonds (and thus are nucleotides) or by other internucleosidic linkages reported in the art, including methylphosphonate, carbonate, oxyacetamide, carbamate, thiophosphate and dithiophosphate internucleosidic linkages.

Further with reference to FIG. 1, 5'-protected nucleoside II is reacted with halohydrocarbylthiophosphoramidite I to form the nucleoside 3'-O-hydrocarbylthiophosphoramidite III. That reaction is typically conducted at room temperature utilizing 2 to 3 fold molar excess of halophosphoramidite I in the presence of a 2 to 4 fold molar excess of a tertiary amine base. The nucleoside 3'-O-hydrocarbylthiophosphoramidite III can be reacted with a nucleoside, for example, a deoxynucleoside of Formula II wherein B is a purine or pyrimidine base, $R_2$ is hydrogen, $R_5$ is protected hydroxyl or solid support and G is hydrogen, to provide a 3'-O-5'-O-dinucleoside hydrocarbylthiophosphite which is subjected to sulfur oxidation to provide the corresponding 3', 5'-dideoxynucleoside dithiophosphate triester illustrated as Formula IV in FIG. 1.

Coupling of the deoxynucleoside ($R_2$=H) 3'-O-thiophosphoramidite III with a 3'-protected hydroxyl-5'-hydroxyl nucleoside can be accomplished in polar aprotic organic solvents, preferably under anhydrous conditions. Anhydrous acetonitrile is a preferred solvent for that coupling reaction. It has been found that the coupling reaction can be effected advantageously in the presence of a nitrogen acid having a pKa equivalent to or greater than tetrazole. The pKa of tetrazole is 4.9. Preferred agents for activating the coupling reaction include nitrogen acids having a pKa between about 4.9 and about 6.0, more preferably between about 4.9 and about 5.5. The term "nitrogen acid" as used herein is an art-recognized term which refers to compounds having a nitrogen atom bonded to a proton which can disassociate with said nitrogen atom and impart acidity to solutions of said compounds. Such compounds include salts, for example, the hydrohalide salts, of tertiary amines including alkylanilines such as dimethylaniline, diisopropylaniline, methylethylaniline, methyldiphenylamine, and pyridine. Nitrogen acids also include nitrogen heterocyclic compounds such as tetrazoles, imidazoles, nitroimidazoles, benzimidazoles, triazoles such as 3,5-dichloro-1,2,4 triazole, and benzotriazoles. Most preferred of the nitrogen acids suitable for use in accordance with this invention is tetrazole.

Recent literature describing the preparation of oligonucleotides containing phosphorodithioate linkages (D. Brill and M. H. Crauthers, Aug. 1988) teach that activating agents more acidic than tetrazole must be used because the coupling reaction stops at the thiophosphoryl-tetrazolide intermediate. The use of more acidic coupling activators as taught by Brill and Crauthers enhances the probability of undesired side reactions such as premature deblocking of protected hydroxyl and amino groups.

Figure 2:
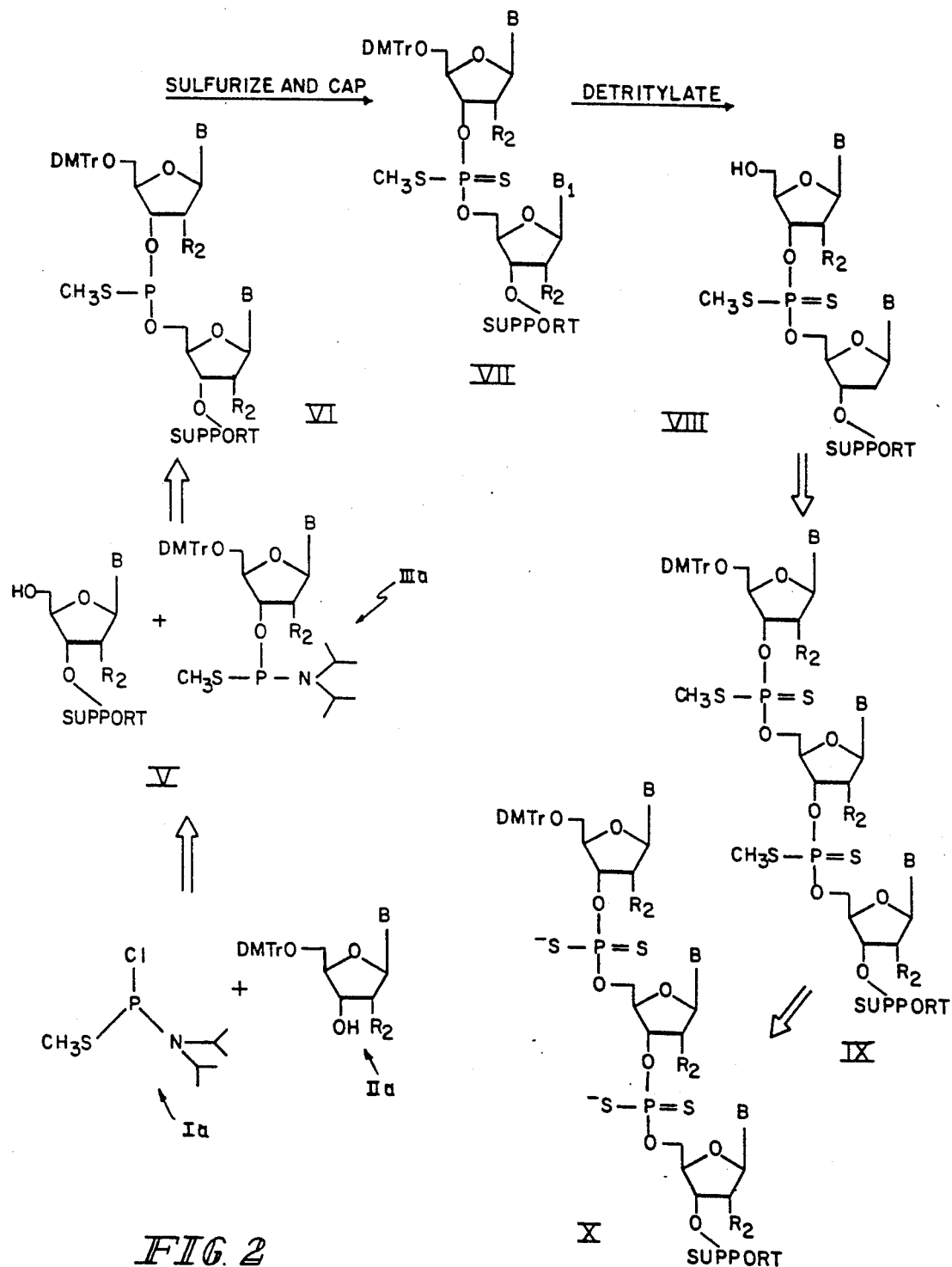
FIG. 2 illustrates a solic phase synthesis scheme for the preparation of nucleoside oligomers having phosphorodithioate internucleosidic linkages; and, FIG. 3 illustrates the overall synthesis of thiophosphoramidite intermediates 2 and 4 and deoxythymidine 6 as set forth in Examples 1 and 2.

Subsequent sulfurization of the dinucleoside thiophosphite intermediate to produce a corresponding dinucleoside dithiophosphate triester IV is carried out typically using elemental sulfur in the presence of an amine base. Subsequent treatment of IV with a source of nucleophilic sulfur such as thiophenol results in removal of the hydrocarbyl group ($R_1$) of Formula IV and production of the corresponding achiral 3',5' dinucleoside phosphorodithioate (not shown). The preparation of nucleoside oligomers having phosphorodithioate internucleosidic linkages using the method of the present invention in a solid phase synthesis scheme is illustrated in FIG. 2.

Chloro-N,N-diisopropylaminothiomethoxyphosphine Ia is reacted with 5'-O-dimethoxytrityl nucleoside IIa to form a 5'-O-dimethoxytrityl nucleoside-3'-thiomethoxyphosphoramidite IIIa. Where the targeted nucleoside oligomer comprises more than one nucleoside, for example, an oligomer IX wherein B in each coupled nucleoside is different, it is advantageous to prepare in advance of initiating the coupling reaction scheme, phosphoramidite intermediates IIIa corresponding to each of the component nucleosides.

Nucleoside phosphoramidite IIIa is reacted with nucleoside V covalently bound to the surface of a solid support through the 3'-hydroxyl moiety. The support is a silica gel, a controlled pore glass, polystyrene, or other art-recognized oligonucleotide support having surface functional groups capable of forming covalent bonds to the nucleoside through its 3'-hydroxy group.

The nature of the surface functional groups used for nucleoside covalent bonding is such that the nucleoside can be released from the solid phase surface under reaction conditions selected to cleave the connecting covalent bonds. The reaction between support bond nucleoside V and intermediate nucleoside phosphoramidite IIIa in the presence of tetrazole provides 3',5'-dinucleoside methylthiophosphite VI. Oxidation of VI with sulfur converts the thiophosphite internucleosidic linkage to a dithiophosphate triester linkage VII. In addition, a so-called capping step is implemented to block any extant 5'-hydroxyl groups on support bound oligonucleoside V that failed to couple with nucleoside phosphoramidite IIIa. The capping step ensures that subsequent reaction cycles will only propagate oligomer chains having the desired nucleoside sequence. Preferred capping agents include acylating reagents such as anhydrides that acylate available unreacted 5'hydroxyl groups. A preferred capping agent is acetic anhydride, typically used in the presence of 4-dimethylaminopyridine.

Detritylation of the support bound dimer VII utilizing a mild acid such as acetic acid, deblocks the 5'-hydroxyl group of the terminal nucleoside. The support bound deblocked dimer can then be subjected to additional nucleoside coupling cycles, each initiated by reaction of the support bound oligomer with a nucleoside thiophosphoramidite IIIa corresponding to the desired nucleoside oligomer sequence. Thus one repetition of the cycle produces support bond trimer IX. Additional repetitions of the coupling cycle can be implemented as necessary to produce the targeted oligomer. As desired, either thiophosphoramidite or phosphoramidite coupling reagents can be utilized to respectively couple nucleosides by dithiophosphate triester linkages or phosphodiester linkages. Treatment of the supported oligomer with thiophenol in the presence of a tertiary amine base converts the internucleosidic dithiophosphate triester linkages to the corresponding phosphorodithioate linkages as shown in Formula X. Isolation of the product oligonucleoside phosphorodithioate analog is accomplished by treatment first to remove hydroxyl and amino protecting groups and secondly to cleave the oligomer from the solid support. Purification of the product can be accomplished using art-recognized DNA purification techniques including gel electrophoresis, high pressure liquid chromatography, or affinity chromatography.

The methods and intermediates in accordance with the present invention are further illustrated by the following examples.

EXAMPLE 1

Figure 3:
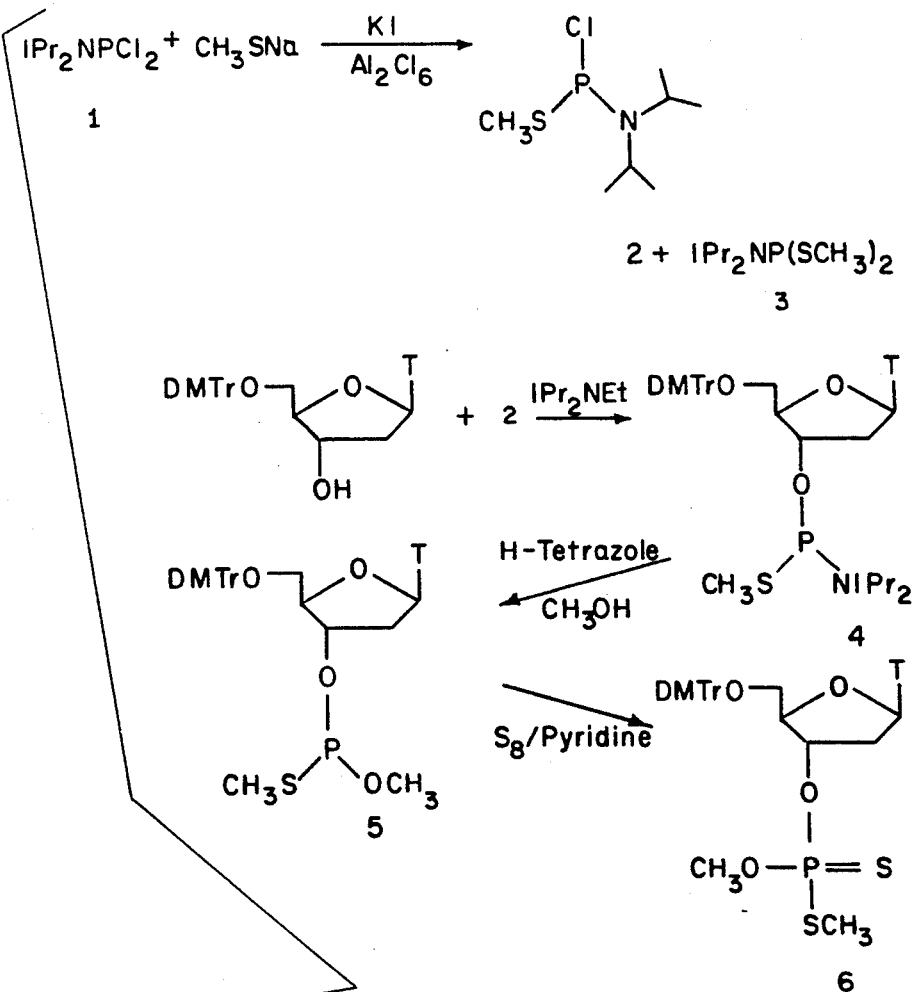

The overall synthesis of the thiophosphoramidite intermediates 2 and 4, and deoxythymidine dithiophosphate 6, is outlined in FIG. 3. Dichloro-N,N-diisopropylaminophosphine 1 was prepared by the reaction of phosphorus trichloride with diisopropylamine (2 equiv). Distillation (56°-59° C./0.5 mmHg) afforded pure phosphine as shown by $^{31}$P NMR ($\delta$ppm in benzene-d$_6$, downfield relative to external 85% H$_3$PO$_4$:169.0).

The synthesis of monochloro-N,N-diisopropylaminothiomethoxyphosphine 2 was accomplished by reacting dichloro-N,N-diisopropylaminophosphine 1 with sodium thiomethoxide (1 equiv) in the presence of aluminum trichloride and potassium iodide. The best yield of the reactive phosphine 2 was obtained by the following procedure. A 50 ml addition funnel was charged with a suspension of sodium thiomethoxide (22.8 mmol) and catalytic amount (2.28 mmol) of potassium iodide in 40 ml of anhydrous dichloromethane. This suspension was added dropwise over a period of 10 hours at −65° C. to a magnetically stirred solution of dichloro-N,N-diisopropylaminophosphine 1 (24.7 mmol) and a catalytic amount of aluminum trichloride (0.5 mmol) in 20 ml of anhydrous dichloromethane. After addition of sodium thiomethoxide the resulting suspension was allowed to stir for 3 hours at −35° C., then 5 hours at −20° C. and finally 10 hours at room temperature. The reaction mixture was then vacuum filtered and the sodium chloride salt was washed with 100 ml anhydrous ether. The filtrate was evaporated under a dry nitrogen atmosphere and reduced pressure (100 mmHg) at room temperature. The purity of the crude residue was checked by $^1$H and $^{31}$P NMR (benzene-d$_6$: chloro-N,N-diisopropylaminothiomethoxyphosphine 2 $\delta^{31}$P 168.0 ppm; N,N-diisopropylaminodithiomethoxyphosphine impurity 3 $\delta$118.2 ppm). The above procedure typically provides 2 in about 95% yield and less than 5% yield of 3 and the crude reaction product used for further reaction without purification.

Crude chloro-N,N-diisopropylaminothiomethoxyphosphine 2 from the above procedure can be stored at −18° C. under an inert, dry atmosphere for at least several months without any decomposition. In contrast, the N,N-diisopropylaminodithiomethoxyphosphine 3 undergoes a Michael-Arbuzov reaction to the extent of roughly 50% after 6 weeks at −18° C. One problem manifested by all monofunctional phosphitylating agents including chloro-N,N-diisopropylaminothiomethoxyphosphine 2 is its sensitivity towards hydrolysis and air oxidation.

Chloro-N,N-diisopropylaminothiomethoxyphosphine 2 was used to prepare the deoxynucleoside thiomethoxyphosphoramidite 4. Excess 2 (5.52 mmol) was added to a mixture of diisopropylethylamine (7.4 mmol), 5'-O-dimethoxytrityl thymidine (1.84 mmol) in 4 ml dichloromethane at room temperature. The complete reaction course was monitored by tlc (silica gel) and by $^{31}$P NM spectroscopy.

After completion of the reaction the mixture was transferred to a separatory funnel and diluted with ethyl acetate. The solution was washed three times with a saturated NaHCO$_3$ solution (25 ml). This was followed by an additional washing with saturated NaCl aqueous solution (25 ml; 3 times). The washing steps were performed under nitrogen at room temperature within 15 minutes. The organic layer was dried over magnesium sulfate overnight and the solvent was evaporated to a foam under reduced pressure. The residue was then taken up in a few ml of dichloromethane and precipitated with 500 ml of ether/n-hexane mixture (−78° C.). This procedure provides N,N-diisopropylamino3'-O-(5'-O-(dimethoxytrityl)thymidine) thiomethoxyphosphine 4 in a 55:45 diastereomeric mixture as indicated by the $^{31}$P NMR spectrum of 4 showing two signals at 164.85 and 163.14 ppm corresponding to a diastereomeric mixture of the thiophosphoramidite. The CI (70 ev) MS analogs of 4 shows a prominent pseudo-molecular ion peak at m/z 722 (M+H)+. Additional intense ions are also observed at m/z 692 (M-2xCH$_3$+H)+, 674 (M-SCH$_3$)+ and 596 (M-1-thyminyl)+. $^1$H NMR (benzene-d$_6$,$\delta$ppm) 1.0 (12H, d, (CH$_3$)$_2$CH)$_2$N), 1.55 (3H, s, thymine-CH$_3$), 2.27 (3H, d, CH$_3$S), 3.30 (6H, s, CH$_3$O), 3.52 (2H, m, 5',5''), 4.20 (1H, br. s, H4'), 4.78 (1H, br. s, H3'), 6.50 (1H, br. m, H1'), 7.20 (13H, m, aromatic).

In addition to the major peaks assigned to 4, there are some minor $^{31}P$ peaks at 146.3 ppm and 13.2 ppm, which are assigned to the 3'-3' nucleoside dimer and a phosphoamidous acid, respectively.

Thiophosphoramidite 4 was coupled with methanol to test the feasibility of the reaction using 1H-tetrazole as a catalyst. The reaction was monitored by $^{31}P$ NMR spectroscopy. Addition of excess methanol and the acid catalyst 1H-tetrazole (0.26 mmol) to a benzene solution of 4 (0.035 mmol) at room temperature resulted in the complete disappearance over several hours of the two $^{31}P$ signals of 4 at 164.85 and 163.14 ppm. The signals are replaced by two new signals at 193.0 and 192.8 ppm (55:45 ratio), which are assigned to a $R_p$ and $S_p$ diastereomeric mixture of 3'-O-methoxythiomethoxyphosphine derivative 5 of 5'-O-(dimethoxytrityl)thymidine.

Oxidation of 5 by sulfur in pyridine generated the dithiophosphate triester 6. $^{31}P$ NMR spectra indicated that the sulfurization reaction was rapid. After 10 minutes at ambient temperatures only about 5% of unreacted 5 remained. The $R_p$ and $S_p$ diastereomeric mixture of dithiophosphate triesters 6 appears as a set of sharp $^{31}P$ NMR resonances at 92.62 and 92.11 ppm (benzene-$d_6$). This is similar to the $^{31}P$ chemical shift for authentic samples of dimethyl and diethyl thiophosphoric acids ($^{31}P$ (benzene $d_6$), 90.05 and 90.67 ppm, respectively). Additional $^{31}P$ signals are observed at 70.97, 68.97, 68.38 ppm, and a number of peaks in the phosphate ester region around 0.0 ppm, the latter presumably arising from desulfurization. Dithiophophpate triester 6 was relatively stable in solvents even at elevated temperatures.

EXAMPLE 2

Thiophosphoramidite 4 was prepared as illustrated in FIG. 3 followed the procedures set forth in Example 1. Thiophosphoramidite 4 was coupled with 3'-O-(t-butyldimethylsilyl) deoxythymidine using 1H-tetrazole as an acid catalyst. The reaction was monitored by $^{31}P$ NMR spectroscopy. Addition of excess 3'-O-(t-butyldimethylsilyl)deoxythymidine and 1H tetrazole (0.26 mmol) to a benzene/acetonitrile solution (1:3) of 4 (0.035 mmol) at room temperature resulted in the complete disappearance over several hours of the two $^{31}P$ signals at 164.85 and 163.14 ppm, and their replacement by two new signals at 190.7 and 191.3 ppm (55:45 ratio), which are assigned to a $R_p$ and $S_p$ diastereomeric mixture of 3'-O-(t-butyldimethylsilyl)-5'-O-deoxythymidinethiomethoxyphosphine derivative of 5'-O-(dimethoxytrityl) thymidine. The best yield of the thiophosphite was obtained by reaction for 60 minutes.

After sulfurization with a large excess of sulfur in pyridine the 3',5'-dideoxythymidine methyl phosphorodithioate triester were observed as two $^{31}P$ signals at 95.7 and 95.4 ppm (benzene-$d_6$). The acetyl protected dithioate triester $^{31}P$ signals appear at 96.8 and 97.2 ppm (benzene-$d_6$). The sulfurization reaction was rapid, and after 10 min. at ambient temperature only about 5% of the unreacted dinucleoside thiophosphite was still present.

S-demethylation of 3',5'-dideoxythymidine methyl phosphorodithioate was accomplished by reaction with thiophenol/diisopropylethyl-amine for 40 hours at room temperature. Removal of the S-protecting methyl group yields the achiral 3',5'-dideoxythymidine phosphorodithioate 114.9 ppm).

EXAMPLE 3

Synthesis of thiophosphoramidites is performed according to the following procedure adapted from Brill et al., J. Am. Chem. Soc.. 111, pp.2321-2322 (1989). Either dipyrrolidinylchlorophosphine or bis-(dimethylamino)chlorophosphine (0.6 mmol) is added to a 5'-O-protected deoxynucleoside (0.5 mmol) in 4 mL of acetonitrile:triethylamine(2:1, v/v). Immediately a precipitate appears. After 5 min, either 4-chlorobenzyl- or 2,4-dichlorobenzylmercaptan (1 mmol) is added, and the reaction mixture is evaporated to a gum. $CH_2Cl_2$: ethyl acetate: TEA (47.5:47.5:5.0) was used to dissolve 0.5 mmol of the crude product. The crude thiophosphoramidite is purified by gravity or flash chromatography using a column of silica gel (320–400 mesh) 5 cm × 1 cm, with the above solvent as eluent. 1.5 ml fractions are collected. The product is observed on TLC as the fastest running compound. Yield was about 70-80% as monitored by P-31 NMR. The solvent of the purified fraction was evaporated under a stream of nitrogen and the last approximately 3 ml of liquid were triturated into n-pentane cooled to 0° C. Product yield can be enhanced by running the synthesis in an inert atmosphere dry box.

EXAMPLE 4

A tetrameric oligonucleotide analog d(Ap($S_2$)GCT) in which the AG phosphate linkage is replaced with a dithiophosphate linkage and a d(C Tp($S_2$) Tp($S_2$) G C T A C T C C Cp($S_2$) Cp($S_2$) A T) corresponding to an antisense oligonucleotide targeted to the arc oncogene were prepared using solid phase synthesis procedures and the reactions exemplified in Examples 1-3 above.

Synthesis of both oligonucleotide analogs was accomplished utilizing the respective thiophosphoramidites (as prepared in Example 3) with a 50-fold excess of tetrazole. Coupling was performed twice to ensure high yields (greater than 98%). A capping acylation of unreacted 5'-hydroxy oligonucleosides, followed by detritylation and oxidation with 5% sulfur in pyridine: carbon disulfide completed the reaction cycle. Each double coupled reaction cycle took approximately 10 minutes. The product oligodeoxynucleotide dithiophosphite triester intermediates were reacted with 5% elemental sulfur in 2,6- lutidine/$CS_2$ for 5-7 minutes followed by $I_2$ oxidation. Repetitions of this cycle utilizing the respective thiophosphoramidites provided precursor dithiophosphite triester intermediates for the above designated oligonucleotide analogs. These dithiophosphite oligonucleotide analogs were reacted with thiopheno:: triethylamine: dioxane (1: 1: 2; v/v/v) for 24 hours followed by reaction with concentrated ammonium hydroxide for 15 hours to convert the internucleosidic dithiophosphite triester linkages to the corresponding phosphorodithioate linkages. The product analogs were purified to homogeneity by standard procedures (polyacrylamide gel electrophoresis and reverse phase HPLC).

The overall yield of d(Ap($S_2$)GCT) was about 80% and that for d(C Tp($S_2$) Tp($S_2$) G C T A C T C C Cp($S_2$) CP($S_2$) A T) was $<10\%$.

We claim:

1. In a method for coupling a first nucleoside or first oligonucleoside having a 5'-hydroxyl and 3'-protected hydroxyl group with a second nucleoside or oligonucleoside having 3'-hydroxyl and a 5'-protected hydroxyl group to form an oligonucleoside coupled through a thiophosphite linkage by reacting said second nucleoside or oligonucleoside with a compound of the formula

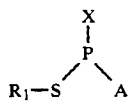

wherein X is chloro, bromo, or a secondary amino group, $R_1$ is a hydrocarbyl radical containing up to 10 carbon atoms, and A is a secondary amino group, to form thiophosphoramidite of the formula

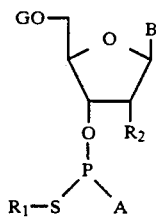

wherein G is selected from the group consisting of a hydroxyl protecting group, a solid support, a nucleoside, a nucleotide and nucleotide analogs; $R_2$ is hydrogen or protected hydroxyl group; B is an amino-protected base; and A and $R_1$ are as defined above; the improvement which comprises reacting said thiophosphoramidite with the first nucleoside or oligonucleoside in the presence of a nitrogen acid having a pKa equivalent to or greater than that of tetrazole.

2. The method of claim 1 wherein the A is a group of the formula $-NR_3R_4$ wherein $R_3$ and $R_4$, taken separately, each represents alkyl, aralkyl, cycloalkyl and cycloalkylalkyl containing up to 10 carbon atoms or $R_3$ and $R_4$, when taken together with the nitrogen atom to which they are attached, form a 5- or 6-membered ring.

3. The method of claim 1 wherein A is diisopropylamino.

4. The method of claim 1 wherein the nitrogenous acid is tetrazole.

* * * * *